US008825161B1

(12) United States Patent
Mi et al.

(10) Patent No.: US 8,825,161 B1
(45) Date of Patent: Sep. 2, 2014

(54) ACOUSTIC TRANSDUCER FOR AN IMPLANTABLE MEDICAL DEVICE

(75) Inventors: Bin Mi, Plymouth, MN (US); Lawrence D. Swanson, White Bear Lake, MN (US); Mark S. Bartrum, Avon, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1397 days.

(21) Appl. No.: 12/122,431

(22) Filed: May 16, 2008

Related U.S. Application Data

(60) Provisional application No. 60/938,571, filed on May 17, 2007.

(51) Int. Cl.
 *A61N 1/08* (2006.01)

(52) U.S. Cl.
 USPC ............................ 607/37; 607/36; 607/61

(58) Field of Classification Search
 USPC .................................. 607/32, 36, 37, 61
 See application file for complete search history.

(56) References Cited

U.S. PATENT DOCUMENTS

| | | |
|---|---|---|
| 2,967,957 A | 1/1961 | Massa |
| 3,568,661 A | 3/1971 | Franklin |
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,832,580 A | 8/1974 | Yamamuro et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |
| 4,051,455 A | 9/1977 | Fowler |
| 4,056,742 A | 11/1977 | Tibbetts |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |
| 4,227,407 A | 10/1980 | Drost |

(Continued)

FOREIGN PATENT DOCUMENTS

| | | |
|---|---|---|
| DE | 3222349 | 1/1984 |
| EP | 0798016 | 10/1997 |

(Continued)

OTHER PUBLICATIONS

Blevins Ph.D., "Formulas for Natural Frequency and Mode Shape", ISBN: 1-57524-184-6.

(Continued)

*Primary Examiner* — Tammie K Heller
(74) *Attorney, Agent, or Firm* — Faegre Baker Daniels LLP

(57) ABSTRACT

An implantable medical device includes a housing defining a hermetically sealed chamber and includes a diaphragm portion having a first resonance frequency, an acoustic communication circuit within the chamber, and an acoustic transducer within the chamber. The transducer includes a substantially rigid pin member attached to an inner surface of the diaphragm portion, and an active portion coupled to the pin member. The active portion has a second resonant frequency and includes a piezoelectric element electrically coupled to the acoustic communication circuit. The diaphragm portion and the active transducer portion may be configured such that the first and second resonance frequencies are substantially equal.

10 Claims, 4 Drawing Sheets

(56) References Cited

U.S. PATENT DOCUMENTS

| | | |
|---|---|---|
| 4,281,484 A | 8/1981 | Massa |
| 4,431,873 A | 2/1984 | Dunn et al. |
| 4,433,400 A | 2/1984 | De Reggi et al. |
| 4,440,983 A | 4/1984 | Facoetti et al. |
| 4,456,850 A | 6/1984 | Inoue et al. |
| 4,471,786 A | 9/1984 | Inagaki et al. |
| 4,481,950 A | 11/1984 | Duggan |
| 4,517,665 A | 5/1985 | De Reggi et al. |
| 4,519,401 A | 5/1985 | Ko et al. |
| 4,541,431 A | 9/1985 | Ibrahim et al. |
| 4,558,249 A | 12/1985 | Lerch et al. |
| 4,577,132 A | 3/1986 | Ohigashi et al. |
| 4,580,074 A | 4/1986 | Gilman |
| 4,593,703 A | 6/1986 | Cosman |
| 4,600,855 A | 7/1986 | Strachan |
| 4,642,508 A | 2/1987 | Suzuki et al. |
| 4,653,036 A | 3/1987 | Harris et al. |
| 4,653,508 A | 3/1987 | Cosman |
| 4,660,568 A | 4/1987 | Cosman |
| 4,672,976 A | 6/1987 | Kroll |
| 4,676,255 A | 6/1987 | Cosman |
| 4,677,337 A | 6/1987 | Kleinschmidt et al. |
| 4,781,715 A | 11/1988 | Wurzel |
| 4,793,825 A | 12/1988 | Benjamin et al. |
| 4,835,435 A | 5/1989 | Yeung et al. |
| 4,846,191 A | 7/1989 | Brockway et al. |
| 4,911,172 A | 3/1990 | Bui et al. |
| 4,940,052 A | 7/1990 | Mann et al. |
| 4,958,100 A | 9/1990 | Crawley et al. |
| 4,992,692 A | 2/1991 | Dias |
| 5,012,815 A | 5/1991 | Bennett, Jr. et al. |
| 5,024,224 A | 6/1991 | Engebretson |
| 5,088,576 A | 2/1992 | Potthoff et al. |
| 5,113,859 A | 5/1992 | Funke |
| 5,160,870 A | 11/1992 | Carson et al. |
| 5,178,153 A | 1/1993 | Einzig |
| 5,283,397 A | 2/1994 | Pavlovic |
| 5,289,821 A | 3/1994 | Swartz |
| 5,300,875 A | 4/1994 | Tuttle |
| 5,304,206 A | 4/1994 | Baker, Jr. et al. |
| 5,314,457 A | 5/1994 | Jeutter et al. |
| 5,339,290 A | 8/1994 | Greenstein |
| 5,367,500 A | 11/1994 | Ng |
| 5,381,067 A | 1/1995 | Greenstein et al. |
| 5,381,386 A | 1/1995 | Lum et al. |
| 5,410,587 A | 4/1995 | Grunwell |
| 5,411,551 A | 5/1995 | Winston et al. |
| 5,423,334 A | 6/1995 | Jordan |
| 5,438,553 A | 8/1995 | Wilson et al. |
| 5,476,488 A | 12/1995 | Morgan et al. |
| 5,483,501 A | 1/1996 | Park et al. |
| 5,488,954 A | 2/1996 | Sleva et al. |
| 5,495,137 A | 2/1996 | Park et al. |
| 5,507,786 A | 4/1996 | Morgan et al. |
| 5,554,177 A | 9/1996 | Kieval et al. |
| 5,562,714 A | 10/1996 | Grevious |
| 5,571,152 A | 11/1996 | Chen et al. |
| 5,628,782 A | 5/1997 | Myers |
| 5,679,026 A | 10/1997 | Fain et al. |
| 5,704,352 A | 1/1998 | Tremblay et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,757,104 A | 5/1998 | Getman et al. |
| 5,776,178 A | 7/1998 | Pohndorf et al. |
| 5,792,195 A | 8/1998 | Carlson et al. |
| 5,807,258 A | 9/1998 | Cimochowski et al. |
| 5,825,117 A | 10/1998 | Ossmann et al. |
| 5,832,924 A | 11/1998 | Archibald et al. |
| 5,833,603 A | 11/1998 | Kovacs et al. |
| 5,843,135 A | 12/1998 | Weijand et al. |
| 5,870,351 A | 2/1999 | Ladabaum et al. |
| 5,873,835 A | 2/1999 | Hastings et al. |
| 5,879,283 A | 3/1999 | Adams et al. |
| 5,935,081 A | 8/1999 | Kadhiresan |
| 5,956,292 A | 9/1999 | Bernstein |
| 5,957,950 A | 9/1999 | Mockros et al. |
| 5,967,986 A | 10/1999 | Cimochowski et al. |
| 6,044,298 A | 3/2000 | Salo et al. |
| 6,053,873 A | 4/2000 | Govari et al. |
| 6,058,329 A | 5/2000 | Salo et al. |
| 6,068,589 A | 5/2000 | Neukermans |
| 6,082,367 A | 7/2000 | Greeninger et al. |
| 6,140,740 A | 10/2000 | Porat et al. |
| 6,141,588 A | 10/2000 | Cox et al. |
| 6,185,452 B1 | 2/2001 | Schulman et al. |
| 6,223,081 B1 | 4/2001 | Kerver |
| 6,353,277 B1 | 3/2002 | Fraunhofer-Gesellschaft |
| 6,409,675 B1 | 6/2002 | Turcott |
| 6,475,170 B1 | 11/2002 | Doron et al. |
| 6,477,406 B1 | 11/2002 | Turcott |
| 6,480,733 B1 | 11/2002 | Turcott |
| 6,486,588 B2 | 11/2002 | Doron et al. |
| 6,504,286 B1 | 1/2003 | Porat et al. |
| 6,504,289 B2 | 1/2003 | Toda |
| 6,527,729 B1 | 3/2003 | Turcott |
| 6,537,200 B2 | 3/2003 | Leysieffer et al. |
| 6,554,761 B1 | 4/2003 | Puria et al. |
| 6,575,894 B2 | 6/2003 | Leysieffer et al. |
| 6,600,949 B1 | 7/2003 | Turcott |
| 6,628,989 B1 | 9/2003 | Penner et al. |
| 6,629,922 B1 | 10/2003 | Puria et al. |
| 6,629,951 B2 | 10/2003 | Laufer et al. |
| 6,643,548 B1 | 11/2003 | Mai et al. |
| 6,645,145 B1 | 11/2003 | Dreschel et al. |
| 6,654,638 B1 | 11/2003 | Sweeney |
| 6,671,550 B2 | 12/2003 | Iaizzo et al. |
| 6,697,674 B2 | 2/2004 | Leysieffer |
| 6,720,709 B2 | 4/2004 | Porat et al. |
| 6,740,076 B2 | 5/2004 | Hoben et al. |
| 6,741,714 B2 | 5/2004 | Jensen |
| 6,763,722 B2 | 7/2004 | Fjield et al. |
| 6,764,446 B2 | 7/2004 | Wolinsky et al. |
| 6,772,490 B2 | 8/2004 | Toda |
| 6,792,308 B2 | 9/2004 | Corbucci |
| 6,999,685 B1 | 2/2006 | Kawase et al. |
| 7,015,392 B1 | 3/2006 | Dickenson |
| 7,016,739 B2 | 3/2006 | Bange et al. |
| 7,024,248 B2 | 4/2006 | Penner et al. |
| 7,035,684 B2 | 4/2006 | Lee |
| 7,107,103 B2 | 9/2006 | Schulman et al. |
| 7,114,502 B2 | 10/2006 | Schulman et al. |
| 7,115,096 B2 | 10/2006 | Siejko et al. |
| 7,118,531 B2 | 10/2006 | Krill |
| 7,123,962 B2 | 10/2006 | Siejko et al. |
| 7,127,290 B2 | 10/2006 | Girouard et al. |
| 7,176,602 B2 | 2/2007 | Schlenke |
| 7,198,603 B2 | 4/2007 | Penner et al. |
| 7,220,232 B2 | 5/2007 | Suorsa et al. |
| 7,228,175 B2 | 6/2007 | Jain et al. |
| 7,236,821 B2 | 6/2007 | Cates |
| 7,248,923 B2 | 7/2007 | Maile et al. |
| 7,260,429 B2 | 8/2007 | Siejko et al. |
| 7,273,457 B2 | 9/2007 | Penner |
| 7,283,874 B2 | 10/2007 | Penner |
| 7,335,169 B2 | 2/2008 | Thompson et al. |
| 7,431,699 B2 | 10/2008 | Siejko et al. |
| 7,522,962 B1 | 4/2009 | Doron et al. |
| 7,580,750 B2 * | 8/2009 | Doron et al. ............... 607/36 |
| 7,615,012 B2 * | 11/2009 | Von Arx et al. ............ 600/528 |
| 7,634,318 B2 | 12/2009 | Tran et al. |
| 8,277,441 B2 | 10/2012 | Porat et al. |
| 8,340,778 B2 | 12/2012 | Tran et al. |
| 2001/0026111 A1 | 10/2001 | Doron et al. |
| 2002/0045921 A1 | 4/2002 | Wolinsky et al. |
| 2002/0062143 A1 | 5/2002 | Baudino et al. |
| 2003/0006673 A1 | 1/2003 | Porat et al. |
| 2003/0014080 A1 | 1/2003 | Baudino |
| 2003/0036746 A1 | 2/2003 | Penner et al. |
| 2004/0106954 A1 | 6/2004 | Whitehurst et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |

(56) References Cited

U.S. PATENT DOCUMENTS

| | | |
|---|---|---|
| 2004/0172079 A1 | 9/2004 | Chinchoy |
| 2004/0230249 A1 | 11/2004 | Haefner |
| 2004/0260214 A1 | 12/2004 | Echt et al. |
| 2005/0131472 A1 | 6/2005 | Ding et al. |
| 2005/0137490 A1 | 6/2005 | Scheiner et al. |
| 2005/0149138 A1 | 7/2005 | Min et al. |
| 2006/0004290 A1 | 1/2006 | Smith et al. |
| 2006/0009818 A1 | 1/2006 | Von Arx et al. |
| 2006/0136004 A1 | 6/2006 | Cowan |
| 2006/0142819 A1 | 6/2006 | Penner et al. |
| 2006/0149329 A1 | 7/2006 | Penner |
| 2007/0049977 A1 | 3/2007 | Von Arx et al. |
| 2007/0055184 A1 | 3/2007 | Echt |
| 2007/0093875 A1 | 4/2007 | Chavan et al. |
| 2007/0142728 A1 | 6/2007 | Penner |
| 2008/0021289 A1 | 1/2008 | Zhang et al. |
| 2008/0021509 A1 | 1/2008 | Mi et al. |
| 2008/0021510 A1 | 1/2008 | Mi et al. |
| 2008/0033497 A1 | 2/2008 | Bulkes et al. |
| 2008/0154135 A1 | 6/2008 | Kimura et al. |
| 2008/0195186 A1 | 8/2008 | Li et al. |
| 2010/0004718 A1 | 1/2010 | Doron et al. |
| 2010/0049269 A1 | 2/2010 | Tran |
| 2010/0094105 A1 | 4/2010 | Porat et al. |
| 2012/0327747 A1 | 12/2012 | Porat et al. |

FOREIGN PATENT DOCUMENTS

| | | |
|---|---|---|
| EP | 0897690 | 2/1999 |
| EP | 1151719 | 11/2001 |
| EP | 1422970 | 5/2004 |
| JP | 57177735 | 11/1982 |
| JP | 60-216697 | 10/1985 |
| JP | 62-073900 | 4/1987 |
| JP | 62102734 | 5/1987 |
| JP | 05023323 | 2/1993 |
| JP | 05-284599 | 10/1993 |
| JP | 07-046694 | 2/1995 |
| JP | 07-301670 | 11/1995 |
| JP | 09-225042 | 9/1997 |
| JP | 09237398 | 9/1997 |
| JP | 10-294995 | 11/1998 |
| JP | 2000-334048 | 12/2000 |
| JP | 2001-514455 | 9/2001 |
| JP | 2002-508682 | 3/2002 |
| JP | 2002-528887 | 9/2002 |
| JP | 2003-079621 | 3/2003 |
| JP | 2003-519542 | 6/2003 |
| JP | 2003-218805 | 7/2003 |
| JP | 2004-147319 | 5/2004 |
| JP | 2006-015137 | 1/2006 |
| JP | 2006-166985 | 6/2006 |
| RU | 2239383 | 11/2004 |
| WO | WO 83/03345 | 10/1983 |
| WO | WO 97/01986 | 1/1997 |
| WO | WO 97/33513 | 9/1997 |
| WO | WO 97/35636 | 10/1997 |
| WO | WO 97/47236 | 12/1997 |
| WO | WO 98/26716 | 6/1998 |
| WO | WO 98/29030 | 7/1998 |
| WO | 9851025 | 11/1998 |
| WO | WO 98-52641 | 11/1998 |
| WO | WO 99/26530 | 6/1999 |
| WO | WO 99/34453 A1 | 7/1999 |
| WO | WO 99/59460 | 11/1999 |
| WO | WO 00/16686 | 3/2000 |
| WO | WO 01-51123 | 7/2001 |
| WO | WO 03/068047 | 8/2003 |
| WO | WO 2004/091719 | 10/2004 |
| WO | WO 2006/069215 | 6/2006 |
| WO | WO 2007/047966 | 4/2007 |

OTHER PUBLICATIONS

C. Hierold et al (Germany, 1998) "Implantable Low Power Integrated Pressure Sensor System for Minimal Invasive Telemetric Patient Monitoring" IEEE, pp. 568-573.

Cassereau et al., "Time Reversal of Ultrasonic Fields—Part 3: Theory of the Closed Time-Reversal Cavity," IEEE Transactions on Ultrasonics, Ferroelectrics, and Frequency Control, vol. 39, No. 5, Sep. 1992, pp. 579-592.

ER. Cosman et al (Massachussetts, Apr. 1979) "A Telemetric Pressure Sensor for Ventricular Shunt Systems" Surgical Neurology, vol. 11, No. 4, pp. 287-294.

Fink et al., "Time Reversal Acoustics," 2004 IEEE Transactions on Ultrasonics, Ferroelectrics, and Frequency Control Joint 50th Anniversary Conference, Ultrasonics Symposium, pp. 850-859.

Fink, "Time Reversal of Ultrasonic Fields—Part 1: Basic Principles," IEEE Transactions on Ultrasonics, Ferroelectrics, and Frequency Control, vol. 39, No. 5, Sep. 1992, pp. 555-566.

G. W. H. Schurink et al (1998) "Late Endoleak after Endovascular Therapy for Abdominal Aortic Aneurysm" Eur. J. Vasc. Endovasc. Surg. vol. 17, pp. 448-450.

GH White et al (1997) "Endoleak Following Endoluminal Repair of AAA: Management Options and Patient Outcomes", J. Endovasc Surg. p. I-45.

Karl E. Richard et al (Germany, Jan. 1999) "First clinical results with a telemetric shunt-integrated ICP-sensor" Neurological Research vol. 21, pp. 117-120.

Prof. Dr. Johannes Zacheja et al (Germany, Sep. 1996) "An Implantable Microsystem for Biomedical Applications" Micro System Technologies 96, pp. 717-722.

S. K. Gupta et al (1999) "Use of a Piezoelectric Film Sensor for Monitoring Vascular Grafts" The American Journal of Surgery vol. 160, pp. 182-186.

T. Chuter et al (Sweden, Jan. 1997) "Aneurysm Pressure following Endovascular Exclusion" Eur. J. Vasc. Endovasc. Surg. vol. 13, pp. 85-87.

T.A. Cochran et al (1990) "Aortic Aneurysm Abdominal", Current Therapy in Adult Medicine, Fourth Edition.

Wu et al., "Time Reversal of Ultrasonic Fields—Part 2: Experimental Results," IEEE Transactions on Ultrasonics, Ferroelectrics, and Frequency Control, vol. 39, No. 5, Sep. 1992, pp. 567-578.

Z. Tang et al (May 1995) "Data Transmission from an Implantable Biotelemeter by Load-Shift Keying Using Circuit Configuration Modulator" IEEE Transactions on Biomedical Engineering, vol. 42, No. 5, pp. 524-528.

\* cited by examiner

ACOUSTIC TRANSDUCER FOR AN IMPLANTABLE MEDICAL DEVICE

CROSS REFERENCE TO RELATED APPLICATION

The present application claims the benefit under 35 U.S.C. §119 of U.S. Provisional Patent Application No. 60/938,571, filed May 17, 2007, entitled "Acoustic Transducer for an Implantable Medical Device" which is incorporated herein by reference in its entirety.

TECHNICAL FIELD

The present invention relates generally to implantable medical systems and particularly, but not by way of limitation, to an implantable medical device including an acoustic transducer for acoustic communications with another device.

BACKGROUND

Implantable medical devices are often used to treat a variety of medical conditions. Examples of implantable medical devices include drug delivery devices, pain management devices, and devices that treat heart arrhythmias. One example of an implantable medical device used to treat heart arrhythmias is a cardiac pacemaker, which is commonly implanted in a patient to treat bradycardia (i.e., abnormally slow heart rate). A pacemaker includes a pulse generator and leads, which form the electrical connection between the pulse generator and the heart. An implantable cardioverter defibrillator (ICD) is used to treat tachycardia (i.e., abnormally rapid heart rate). An ICD also includes a pulse generator and leads that deliver electrical energy to the heart. Pulse generators typically include a metallic housing for a battery and electrical circuitry and a header for connecting the leads to the pulse generator.

Implantable medical devices are also useful in the treatment of heart failure. For example, cardiac resynchronization therapy (CRT) (also commonly referred to as biventricular pacing) is an emerging treatment for heart failure, which involves stimulation of both the right and left ventricles to increase hemodynamic efficiency and cardiac output. The treatment of heart failure and heart arrhythmias can be enhanced through the use of remote implanted devices. One example of such a remote device is a pressure sensor located in the vasculature. Communication between the implantable medical device and the remote device can allow the sensor data to be downloaded by a clinician used to modify the therapy delivered by the implantable medical device, or both.

SUMMARY

The present invention, in one embodiment, is an implantable medical device configured for acoustic communication with a second device. The implantable medical device includes a housing defining a hermetically sealed chamber having an inner surface, and an acoustic communication circuit disposed within the chamber. The implantable medical device further comprises a generally annular ring member attached to the inner surface of the housing, the ring member having an inner diameter defining a diaphragm portion of the housing, a generally planar first piezoelectric element electrically coupled to the communication circuit, a generally planar, flexible disk member attached to and electrically isolated from the first piezoelectric element, and a substantially rigid pin member extending between the disk member and the diaphragm portion of the housing. The pin member includes a first end attached to the inner surface in the diaphragm portion, and a second end opposite the first end and coupled to the disk member. The pin member is operable to transmit induced mechanical vibrations between the diaphragm portion and the disk member without undergoing deformation.

In various embodiments, the disk member has an outer diameter of from about 10 mm to about 25 mm and a thickness of from about 0.2 mm to about 1 mm, the pin member has an outer diameter of from about 1 mm to about 5 mm and a height of from about 0.5 mm to about 3 mm, and the piezoelectric element has an outer diameter of from about 5 mm to about 25 mm.

In various embodiments, the disk member and the pin member are made of titanium, titanium alloys, or stainless steel, and the ring member is made from stainless steel, titanium or a titanium alloy, or tungsten or a tungsten alloy, and has an inner diameter of from about 10 mm to about 25 mm. In one particular embodiment, the diaphragm portion has a thickness of about 0.3 mm, the ring member has an inner diameter of about 16 mm and a height of about 2 mm, the pin member has an outer diameter of about 2.5 mm and a height of about 1 mm, the disk member has an outer diameter of about 11.7 mm and a thickness of about 0.5 mm, and the piezoelectric element has an outer diameter of about 6 mm and a thickness of about 0.5 mm.

In various embodiments, the flexible disk member has a first surface and a second surface opposite the first surface, wherein the first piezoelectric element is attached to an electrically isolated from the first surface. In one such embodiment, the device further comprises a second piezoelectric element attached to and electrically isolated from the second surface of the disk member. In various embodiments, the first and second piezoelectric elements are generally annular each including a central opening, whereby the pin member, the disk member, and the piezoelectric elements are arranged substantially coaxially, and the second end of the pin member extends through the central opening of the second piezoelectric element. In exemplary embodiments, the disk member has an outer diameter of from about 10 mm to about 30 mm and a thickness of from about 0.2 mm to about 1 mm, the pin member has an outer diameter of from about 1.5 mm to about 5 mm and a height of from about 0.5 mm to about 3 mm, and the piezoelectric elements each have an outer diameter of from about 5 mm to about 15 mm. Additionally, in various embodiments, the disk member and the pin member are made of titanium, a titanium alloy, or stainless steel, and the ring member is made from stainless steel, titanium or a titanium alloy, or tungsten or a tungsten alloy, and has an inner diameter of from about 10 mm to about 25 mm.

In one particular embodiment, the diaphragm portion has a thickness of about 0.3 mm, the ring member is made from a tungsten alloy and has an inner diameter of about 16 mm and a height of about 2 mm, the pin member has an outer diameter of about 2.5 mm and a height of about 2.26 mm, the disk member has an outer diameter of about 11.6 mm and a thickness of about 0.5 mm, and the piezoelectric elements each have an outer diameter of about 8 mm and a thickness of about 0.3 mm.

The present invention, in another embodiment, is an implantable medical device comprising a housing defining a hermetically sealed chamber, the housing having an inner surface and a diaphragm portion of the housing having a first resonance frequency. The implantable medical device further comprises an acoustic communication circuit within the chamber, and an acoustic transducer within the chamber. The acoustic transducer includes a substantially rigid pin member having a first end attached to the inner surface in the diaphragm portion and a second end opposite the first end, and an active portion coupled to the second end of the pin member. The active portion is electrically coupled to the acoustic communication circuit and has a second resonance frequency.

In various embodiments, the diaphragm portion, the acoustic communication circuit, and the acoustic transducer form an acoustic communication system, wherein the first and second resonance frequencies are selected so as to control at least one frequency response characteristic of the acoustic communication system. In one embodiment, the frequency response characteristic is a transmit sensitivity. In one such embodiment, the first and second resonance frequencies are substantially equal.

In various exemplary embodiments, the active portion includes a generally planar, flexible disk member having a first surface and a second surface opposite the first surface, and first and second generally planar, annular piezoelectric elements attached to and electrically isolated from the first and second surface of the disk member, respectively, and electrically coupled to the communication circuit, wherein the second end of the pin member is attached to the second surface of the disk member. In one such embodiment, one or more of the pin member, the disk member, the first and second piezoelectric elements, and the diaphragm portion are configured such that first and second resonant frequencies are substantially equal. In one embodiment, the first and second resonance frequencies are about 40 KHz.

In yet another embodiment, the present invention is a cardiac rhythm management (CRM) system comprising an implantable CRM device adapted for implantation in a body of a patient. The CRM device includes a housing defining a hermetically sealed chamber, the housing having an inner surface and a diaphragm portion having a first resonance frequency and being adapted to respond to induced mechanical vibrations, an acoustic communication circuit within the chamber, and an acoustic transducer within the chamber including an active portion electrically coupled to the communication circuit and mechanically coupled to the diaphragm portion by a substantially rigid pin member. The active portion has a second resonance frequency. The CRM system further comprises a second device acoustically coupled to the CRM device, wherein the acoustic transducer and the diaphragm portion are operable to transmit acoustic signals to and receive acoustic signals from the second device. The acoustic signals have a communication carrier signal frequency. In one exemplary embodiment, the active portion includes a generally planar, flexible disk member coupled to the pin member and having first and second surfaces, a generally planar first piezoelectric element attached to and electrically isolated from the first surface of the disk member and electrically coupled to the acoustic communication circuit, and a second piezoelectric element attached to and electrically isolated from the second surface of the disk member. In exemplary embodiments, the first and second resonance frequencies are substantially equal to the communication signal carrier frequency.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
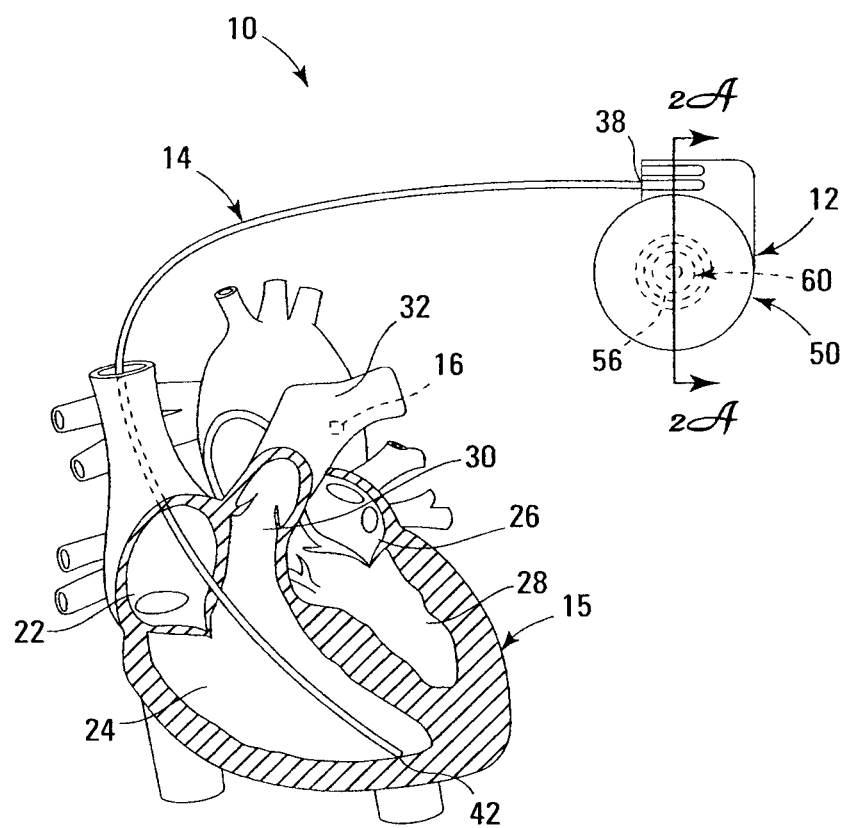
FIG. 1 is a schematic drawing of a cardiac rhythm management (CRM) system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a CRM system 10 according to one embodiment of the present invention. As shown in FIG. 1, the CRM system 10 includes a pulse generator 12 coupled to a lead 14 deployed in a patient's heart 15, and a remote device 16. As is known, the heart 15 includes a right atrium 22 and a right ventricle 24, a left atrium 26 and a left ventricle 28. As shown, the right ventricle 24 includes an outflow tract 30 leading to a pulmonary artery 32. As will be explained in detail below, the remote device 16 and the pulse generator 12 are communicably coupled for exchanging data and/or commands wirelessly via acoustic telemetry.

As will be appreciated, the pulse generator 12 is typically implanted subcutaneously at an implantation location in the patient's chest or abdomen. As shown, the lead 14 includes a proximal end 38 coupled to the pulse generator 12 and a distal end 42 implanted in the right ventricle 24. The lead 14 operates to convey electrical signals between the heart 15 and the pulse generator 12. For illustrative purposes only, the CRM system 10 is shown having only the single lead 14. It will be appreciated, however, that CRM systems such as the CRM system 10 may typically include a plurality of leads implanted so as to electrically stimulate other areas of the heart. For example, in various embodiments, a second lead (not shown) may be utilized with its distal end implanted in the right atrium 22. Additionally, in some embodiments, another lead may be implanted to facilitate stimulation of the left side of the heart 15 (i.e., to stimulate the left ventricle 28). In some embodiments, the CRM system 10 may include one or more epicardial leads in lieu of or in addition to the lead 14. In short, any configuration of leads for stimulating heart tissue, whether now known or later developed, may be utilized with the CRM system 10.

As shown, the pulse generator 12 includes a housing 50 which operates as a hermetically-sealed enclosure for the pulse generator circuitry and components. The housing further includes a diaphragm portion 56 which, as described in detail below, is a resonant structure which provides a higher efficiency for the acoustic telemetry as compared to other portions of the housing 50. Additionally, the pulse generator 12 includes an acoustic transducer 60 enclosed by the housing 50 and mechanically coupled to the diaphragm portion 56. As will be explained in detail below, the acoustic transducer 60 is adapted to generate and receive acoustic waves for acoustic communication with, in the illustrated embodiment, the remote device 16. In other embodiments, the acoustic transducer 60 may be utilized to facilitate acoustic communication between the pulse generator 12 and other remote devices (not shown) or devices located external to the patient's body. Thus, in the various embodiments of the present invention, the combined structure of the diaphragm portion 56 and the acoustic transducer 60 form an acoustic transmitter/receiver operable to transmit and receive acoustic waves for acoustic communication with other devices.

The pulse generator 12 may be any implantable medical device known in the art or later developed, for delivering an electrical therapeutic stimulus to the patient. In one embodiment, the pulse generator 12 is a pacemaker. In another embodiment, the pulse generator 12 is an implantable cardiac defibrillator. In still other exemplary embodiments, the pulse generator 12 includes both pacing and defibrillation capabilities.

The remote device 16 may be configured to perform one or more designated functions, which may include taking one or more physiological measurements. The remote device 16 may be configured to measure any known physiologic parameters such as, for example, blood pressure, temperature, blood or fluid flow, strain, electrical, chemical, or magnetic properties within the body. The specific functions for the remote device 16 are determined based on the particular therapeutic needs of the patient. In the illustrated embodiment, the remote device 16 is implanted in the main pulmonary artery 32, and includes a pressure sensor for sensing pulmonary arterial pressure. In other embodiments, the remote device 16 including a pressure sensor assembly may be implanted in a branch of the pulmonary artery 32 (e.g., the right or left pulmonary artery). In such embodiments, for example, the sensed pressure can be used to predict decompensation of a heart failure patient or to optimize pacing and/or defibrillation therapy.

It is emphasized, however, that in various other embodiments, the remote device 16 may be implanted in other regions of the patient's vasculature or in other body lumens, and may comprise any type of chronically implanted device or remote sensor adapted to deliver therapy or monitor biological functions. For example, the remote device 16 could comprise a volume sensor or sense any other cardiac parameter, such as maximum or minimum pressure, or calculate a cardiac parameter derivative, such as the slope of the pressure. In other embodiments, the remote device 16 could comprise a glucose level monitor, a pulmonary sound sensor, a satellite pacing device, or any other remote sensing or therapy-delivering device. A plurality of remote devices 16 could be implanted throughout the body and be configured for wireless communication with each other and with the pulse generator 12 or another implanted medical device.

Figure 2A:
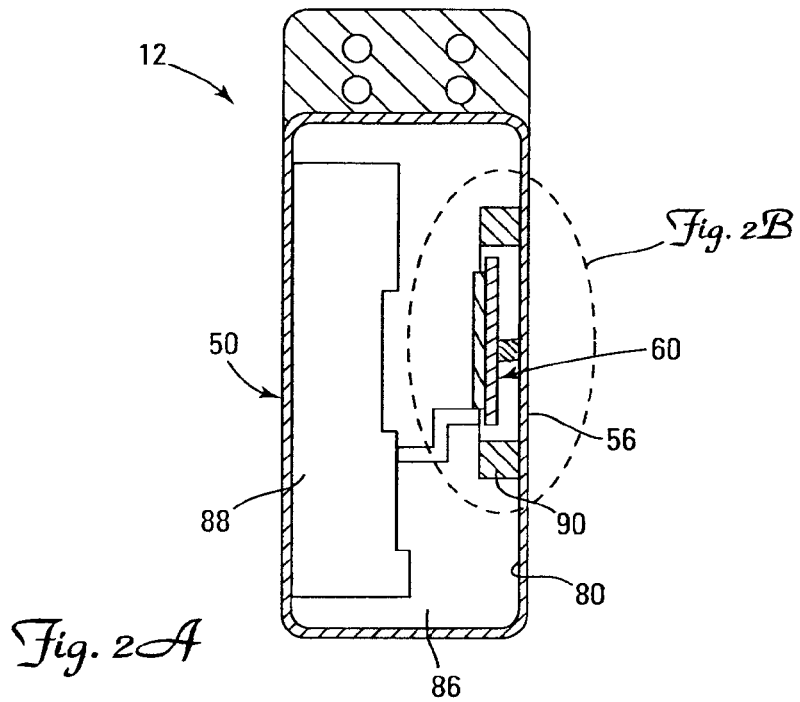
FIGS. 2A and 2B are partial cross-sectional schematic views of a pulse generator for the CRM system of FIG. 1 including an exemplary acoustic transducer according to one embodiment of the present invention.
Figure 2B:
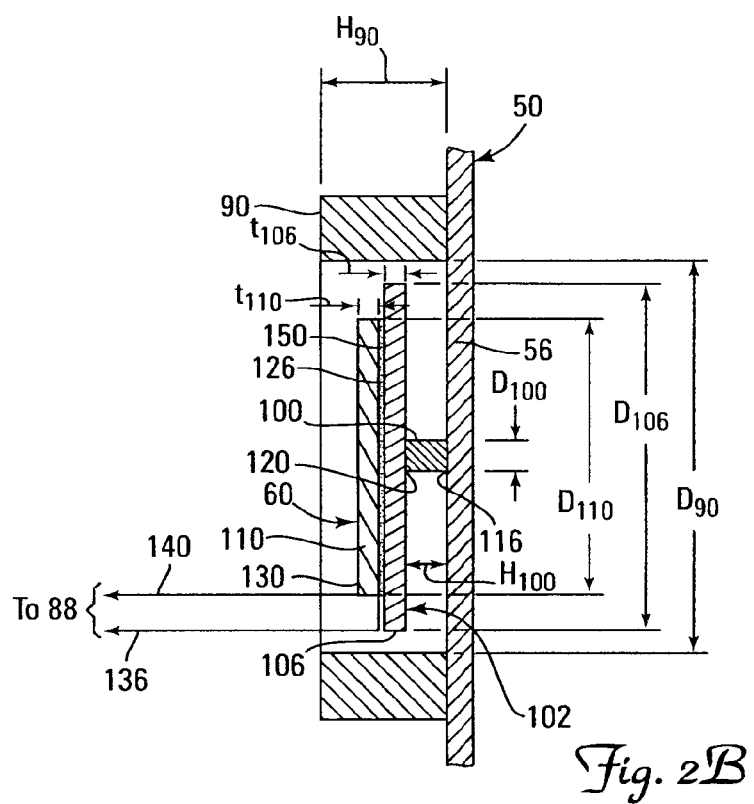

FIGS. 2A and 2B are partial cross-sectional schematic views of the pulse generator 12. As shown in FIG. 2A, the pulse generator housing 50 includes an inner surface 80 and defines a chamber 86 within which the pulse generator circuitry and components, including communication circuitry 88 and the acoustic transducer 60, are disposed. As further shown, the acoustic transducer 60 is attached to the inner surface 80 in the diaphragm portion 56. In the illustrated embodiment, the pulse generator 12 includes a ring member 90 attached to the inner surface 80 and having an inner diameter $D_{90}$. The ring member 90 is, in one embodiment, generally stiff and rigid, such that the inner diameter $D_{90}$ defines the diaphragm portion 56 of the housing 50.

As shown in FIG. 2B, the acoustic transducer 60 includes a pin member 100 and an active portion 102 including a generally planar, flexible disk member 106, and a piezoelectric element 110. The pin member 100 includes opposed ends 116, 120, with the end 116 attached to the diaphragm portion inner surface 80, and the second end 120 coupled to the flexible disk 106. The piezoelectric element 110 includes opposed sides 126, 130, and a pair of electrodes 136, 140 electrically connected to the sides 126, 130, respectively, and also to the communication circuitry 88, so as to electrically couple the acoustic transducer 60 and the communication circuitry 88. As further shown, the piezoelectric element 110 is attached to the flexible disk member 106 opposite the pin member 100. Additionally, an electrical insulating layer 150 is disposed between and electrically isolates the piezoelectric element 110 and the flexible disk member 106. As will be explained in detail below, the pin member 100 operates to mechanically couple the active portion 102 to the diaphragm portion 56 of the housing (i.e., to transmit mechanical vibrations between the active portion 102 of the transducer 60 and the diaphragm portion 56 of the housing 50).

As shown, the pin member 100, the flexible disk member 106, and the piezoelectric element 110 are arranged coaxially, and the acoustic transducer 60 is substantially centered in the diaphragm portion 56 of the housing 50. In the illustrated embodiment, the piezoelectric element 110 and the flexible disk member 106 are generally planar structures (i.e., have generally rectangular cross-sectional shapes). In other embodiments, one or both of the flexible disk member 106 and the piezoelectric element 110 may have at least one non-planar surfaces.

The principles of operation of piezoelectric transducers are well known, and are not discussed in detail herein. In short, the application of an AC voltage across the electrodes 136, 140, i.e., using the pulse generator 12 power supply (not shown) and the communication circuitry 88, causes the piezoelectric element 110 to vibrate at the frequency of the applied voltage. In the acoustic transducer 60, such vibrations are transmitted via the pin member 100 to the diaphragm portion 56 of the housing 50, thereby causing the diaphragm portion 56 to vibrate at the same frequency as the driving voltage. As will be appreciated, these vibrations are then transmitted to the remote device 16 (or an external device) via the acoustic couple provided by the patient's bodily fluids.

Conversely, acoustic waves or signals transmitted from the remote device 16 (or an external device) will induce mechanical vibrations of the diaphragm portion 56, which induced mechanical vibrations will be transmitted to the active portion 102 of the transducer by the pin member 100. As will also be appreciated, such induced mechanical vibrations of the piezoelectric element 110 will cause a voltage change or a charge density change across the piezoelectric element 110, which is detected by communication circuitry 88. Accordingly, the acoustic transducer 60 can operate as both an acoustic transmitter and receiver for acoustic communication between the pulse generator 12 and the remote device 16 (or other remote or external devices). Thus, the diaphragm portion 56, the acoustic transducer 60, and the communication circuitry 88 form an acoustic communication system for the pulse generator 12.

According to the various embodiments of the present invention, the diaphragm portion 56 and the active portion 102 of the acoustic transducer 60 are resonant structures, and each can be configured to have a predetermined resonance frequency. Inclusion of the pin member 100 facilitates a transducer design in which the resonance frequencies of the active portion 102 and the diaphragm portion 56 can be tailored to control the frequency response characteristics of the acoustic communication system for optimizing the performance of the acoustic communication system. Additionally, in various embodiments, the pin member 100 can be configured to have an insubstantial effect on the resonance frequencies of the active portion of the transducer 60 and the diaphragm portion 56 of the housing.

For example, the resonance frequency of the diaphragm portion 56 can be predetermined by selecting appropriate values for the inner diameter $D_{90}$ of the ring 90 and the wall thickness of the housing 50. Similarly, the resonance frequency of the active portion 102 of the transducer 60 can be predetermined based on the selected outer diameter and thickness of the flexible disk member 106 and/or the piezoelectric element 110. In one embodiment, the diaphragm portion 56 and the active portion 102 can be configured such that their resonance frequencies are substantially equal, such that the resulting acoustic communication system will have high transmit and receive sensitivities as compared to conventional acoustic transducer designs. In one embodiment, the resonance frequencies of the diaphragm portion 56 and the transducer active portion 102 are selected to be substantially equal to the acoustic communication carrier frequency.

In another embodiment, the active portion 102 of the acoustic transducer 60 and the diaphragm portion 56 of the housing 50 are configured such that the overall diaphragm/transducer structure (i.e., the acoustic transmitter/receiver) has a predetermined resonance frequency. In one embodiment, this acoustic transmitter/receiver resonance frequency may be selected to be substantially equal to the acoustic communication carrier frequency.

In other embodiments, the diaphragm portion 56 and the active portion 102 of the acoustic transducer 60 may be configured to have resonance frequencies that are intentionally mismatched by a predetermined amount, with the communication carrier frequency falling between the respective resonance frequencies of the diaphragm portion 56 and the active transducer portion 102. Such an embodiment results in an acoustic communication system having an increased bandwidth, but decreased sensitivity, as compared to the embodiment just described.

In the various embodiments of the present invention, the active portion 102 of the transducer 60 is configured to achieve improved frequency response as compared to prior designs in which the transducer is coupled over its entire extent to the diaphragm (i.e., is not offset from the diaphragm by a pin member). For example, in the various embodiments, use of the flexible disk 106 and offsetting the active portion 102 from the diaphragm portion 56 by the pin member 100 allows the active portion 102 to undergo relatively large displacements when excited by an electrical stimulus or by acoustic energy. As a result, the transducer 60 can achieve high sensitivities at higher resonance frequencies as compared to conventional designs.

As mentioned above, in some embodiments, the pin member 100 may be configured to have an insubstantial effect on the resonance frequencies of the diaphragm portion 56 and/or the active portion 102. For example, in one embodiment, the pin member 100 may be designed to have a low mass and an outer diameter $D_{100}$ that is substantially smaller than the inner diameter $D_{90}$ of the ring member 90 such that the pin member 100 does not appreciably effect the stiffness of either the diaphragm portion 56 or the active transducer portion 102. At the same time, the pin member 100 may yet still be designed to be substantially stiff and rigid such that it does not deform in response to induced mechanical vibrations of the diaphragm portion 56 or the active transducer portion 102. In such an embodiment, the pin member 100 operates substantially exclusively to transmit induced mechanical vibrations between the diaphragm portion 56 and the active transducer portion 102 without otherwise significantly affecting the characteristics or performance of these components or the acoustic communication system.

In some embodiments, to increase the robustness of the acoustic transducer 60, it may be desirable to increase the diameter of the pin member 100 at least at its first end 116, which is attached to the diaphragm portion inner surface 80. For example, in one embodiment, the pin member 100 may include a pad or foot (not shown) at opposed end 116 having a larger diameter than the diameter of the pin member 100 in general. Such a design may advantageously increase the stability of the connection of the pin member 100 to the diaphragm portion 56. It will be appreciated that in such embodiments, the configuration of the diaphragm portion 56 and/or the active transducer portion 102 and in particular, the flexible disk member 106 may further be adjusted to compensate for the effect of the pin member 100 on the resonance frequencies of the diaphragm portion 56 and/or the active transducer portion 102.

The piezoelectric element 110 may be made from any piezoelectric material, whether now known or later developed. Such piezoelectric materials include, without limitation, piezo polymer, piezo crystal, or piezo ceramic materials. In one embodiment, the piezoelectric element 110 may be made substantially of polyvinylidine difluoride (PVDF). In another embodiment, the piezoelectric element 110 may be made substantially of lead zirconate titanate (PZT). In yet another embodiment, the piezoelectric element 110 may be made substantially of a piezo single crystal material, such as lead magnesium niobate-lead titanate (PMN-PT). Still other suitable piezoelectric materials for use in the piezoelectric element 110 will be apparent to those skilled in the art based on the foregoing.

The insulating layer 150 may be made from any suitable electrically insulative material known in the art. In one embodiment, the insulating layer 150 may be made substantially from a polyimide material. Other insulating layer materials will be readily apparent to those skilled in the art.

The materials for the diaphragm portion 56, the ring member 90, the pin member 100, and the flexible disk member 106 may be selected to provide the desired acoustic communication system characteristics. In some embodiments, the diaphragm portion 56 may be formed from the same material as the housing 50 in general, and may be defined by the ring member 90 attached to the inner surface 80. The housing 50 in general may be made from any of a range of biocompatible materials suitable for forming the hermetic housing for implantable medical devices. Commonly used materials for such purposes are titanium and titanium alloys. Accordingly, in the embodiments just mentioned, the diaphragm portion 56 is also made from titanium or a titanium alloy and has the same wall thickness as the housing 50 in general. In one embodiment, the diaphragm portion 56 is made from a different biocompatible material than the housing 50 in general.

The ring member 90, the pin member 100, and the disk member 106 may be made from a variety of metallic or non-metallic materials. For example, in various embodiments, the ring member 90 may be made from, without limitation, stainless steel, titanium and/or titanium alloys, aluminum and/or aluminum alloys, and tungsten and/or tungsten alloys. In one embodiment, the pin member 100 and/or the disk member 106 may be made from stainless steel, aluminum and/or aluminum alloys, titanium and/or titanium alloys. In one embodiment, the pin member 100 and the disk member 106 are coupled together as a monolithic structure formed, e.g., machined, from the same material. In other embodiments, the pin member 100 and the disk member 106 may initially be formed as separate elements and may be coupled or attached together using joining methods known in the art, e.g., welding, brazing, soldering, or adhesive bonding.

The ring member 90 and the pin member 100 may be attached to the inner surface 80 of housing 50 using any joining techniques known in the art. In various embodiments, such techniques include welding, brazing, soldering, and adhesive bonding. In one embodiment, the housing 50, including the diaphragm portion 56, and the pin member 100 are both made from titanium or the same titanium alloy, and the pin member 100 is attached to the inner surface 80 by a welding process (e.g., spot or laser welding). In one embodiment, the housing 50 and the pin member 100 are made from dissimilar materials, and are attached together using an adhesive bond or other non-welded joining method, e.g., brazing or soldering.

As discussed above, the resonance frequencies of the diaphragm portion 56 and the active transducer portion 102 may, in various embodiments, be pre-determined to provide the desired frequency response characteristics for the acoustic communication system. In one embodiment, the diaphragm portion 56, the pin member 100, and the active transducer portion 102 are configured such that, in the assembled pulse generator 12, the diaphragm portion 56 and the active transducer portion 102 have the same resonance frequencies substantially corresponding to the acoustic communication carrier frequency. In various embodiments, the diaphragm portion 56 has a diameter (corresponding to the ring 90 inner diameter $D_{90}$) of from about 10 mm to about 25 mm, the disk member 106 has an outer diameter $D_{106}$ of from about 10 mm to about 30 mm and a thickness $t_{106}$ of from about 0.2 mm to about 1 mm, the pin member 100 has an outer diameter $D_{100}$ of from about 1 mm to about 5 mm and a height $H_{100}$ of from about 0.5 mm to about 3 mm, and the piezoelectric element 110 has an outer diameter $D_{110}$ of from about 5 mm to about 25 mm and a thickness $t_{110}$ of from about 0.2 mm to about 1 mm.

In one embodiment, the acoustic communication carrier frequency is about 20 KHz or higher. In one embodiment, the acoustic communication carrier frequency is about 40 KHz. In one embodiment, described in Table 1 below, the diaphragm portion 56 and the acoustic transducer active portion 102 are configured to be resonant at the 40 KHz communication carrier frequency, as determined by the following system characteristics:

TABLE 1

| Diaphragm 56 | |
| --- | --- |
| Material | titanium |
| Thickness $t_{56}$ | 0.3 mm |
| Ring member 90 | |
| Material | 303 stainless steel |
| Inner diameter $D_{90}$ | 16 mm |
| Height $H_{90}$ | 2 mm |
| Pin member 100 | |
| Material | 6AL4V ELI titanium alloy |
| Outer diameter $D_{100}$ | 2.5 mm |
| Height $H_{100}$ | 1 mm |
| Disk member 106 | |
| Material | 6AL4V ELI titanium alloy |
| Outer diameter $D_{106}$ | 11.7 mm |
| Thickness $t_{106}$ | 0.5 mm |

TABLE 1-continued

| Piezoelectric element 110 | |
| --- | --- |
| Material | PZT 5K |
| Outer diameter $D_{110}$ | 6 mm |
| Thickness $t_{110}$ | 0.5 mm |

In the foregoing embodiment, the coupled acoustic transducer 60 and diaphragm portion 56 are predicted to provide an acoustic communication system having a relatively high transmit sensitivity of at least about 200 Pa/V at 25 cm of water.

Figure 3A:
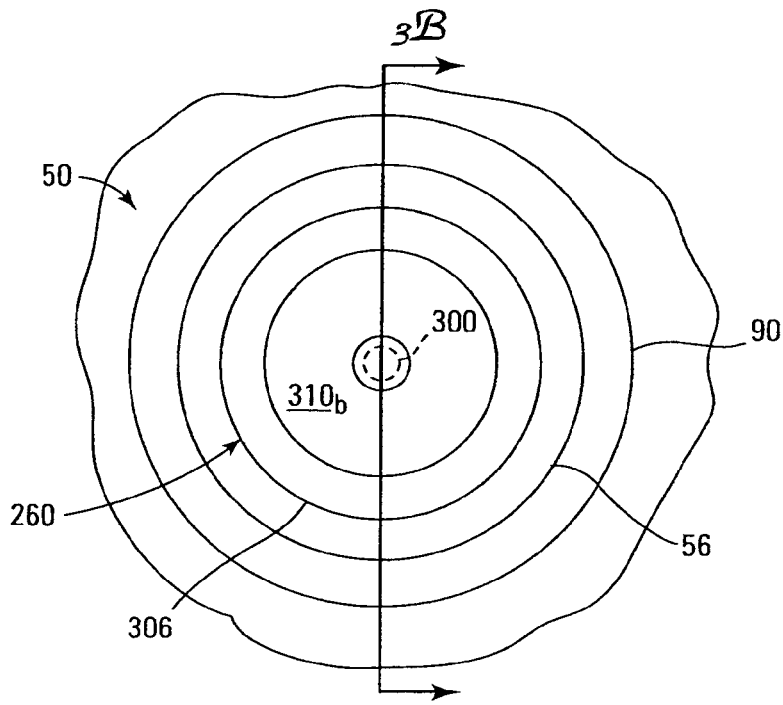
FIGS. 3A and 3B are front and cross-sectional views of an alternative acoustic transducer incorporated into the pulse generator for the CRM system of FIG. 1 according to one embodiment of the present invention.
Figure 3B:
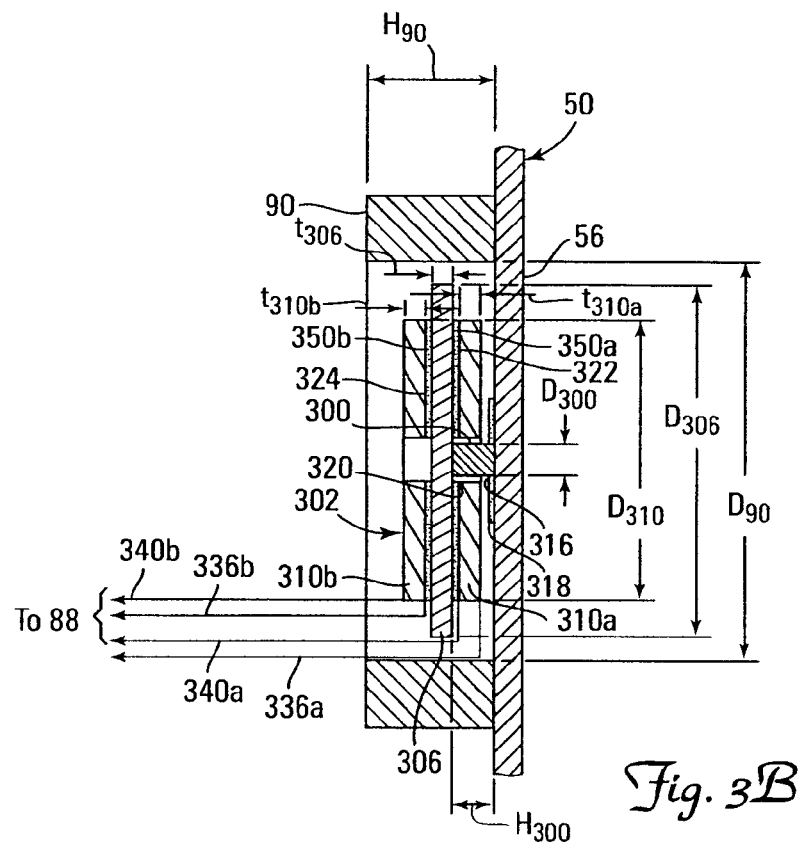

FIGS. 3A and 3B are front and cross-sectional views of an alternative acoustic transducer 260 fastened to the diaphragm portion 56 of the pulse generator housing 50 according to another embodiment of the present invention. As shown in FIGS. 3A and 3B, the transducer 260 includes a pin member 300 and an active portion 302 including a flexible disk member 306 and dual piezoelectric elements 310a, 310b. The pin member 300 includes opposed ends 316, 320, with the end 316 including a pad 318 attached to the diaphragm portion inner surface 80, and the end 320 coupled to the flexible disk member 306. The piezoelectric elements 310a, 310b are generally annular and are attached to respective surfaces 322, 324 of the flexible disk member 306. As further shown, electrodes 336a, 340a, and 336b, 340b are electrically connected to opposed sides of the piezoelectric elements 310a, 310b, respectively, and to the communication circuitry (not shown) of the pulse generator 12. Additionally, electrical insulating layers 350a, 350b are disposed between and electrically isolate the piezoelectric elements 310a, 310b, respectively, and the flexible disk member 306. In the illustrated embodiment, the piezoelectric elements 310a, 310b are electrically coupled in parallel, although this is not a requirement.

As can be best seen in FIG. 3B, the piezoelectric element 310b is generally annular so as to accommodate the end 320 of the pin member 300, which extends through the center opening of the piezoelectric element 310b. Accordingly, because the piezoelectric elements 310a, 310b are desirably made symmetrical to enhance the performance and stability of the transducer 260, the piezoelectric element 310a is also generally annular. In various embodiments, the piezoelectric elements 310a, 310b have substantially the same or identical physical dimensions and are made from substantially the same or identical materials.

The pin member 300, the disk member 306, and the piezoelectric elements 310a, 310b provide substantially the same or identical functionality as the corresponding elements of the acoustic transducer 60 described above. Accordingly, the pin member 300, the disk member 306, and the piezoelectric elements 310a, 310b may, in various embodiments, be made any of the same materials described above in connection with the pin member 100, the disk member 106, and the piezoelectric element 110. In the illustrated embodiment, the pad 318 is provided to enhance the robustness of the connection between the pin member 300 and the diaphragm portion 56 of the housing 50. In other embodiments, however, the pad 318 is omitted.

As with the pulse generator 12 including the acoustic transducer 60 discussed above, the resonance frequencies of the diaphragm portion 56 and the active transducer portion 302 may, in various embodiments, be pre-determined to provide the desired frequency response characteristics for the acoustic communication system. In one embodiment, the diaphragm portion 56, the pin member 300, and the active transducer portion 302 are configured such that, in the assembled pulse generator 12, the diaphragm portion 56 and the active transducer portion 302 have the same resonance frequencies substantially corresponding to the acoustic communication carrier frequency. In various embodiments, the diaphragm portion 56 has a diameter (corresponding to the ring 90 inner diameter $D_{90}$) of from about 10 mm to about 25 mm, the disk member 306 has an outer diameter $D_{306}$ of from about 10 to about 30 mm and a thickness $t_{306}$ of from about 0.2 mm to about 1 mm, the pin member 300 has an outer diameter $D_{300}$ of from about 1.5 mm to about 5 mm and a height $H_{300}$ of from about 0.5 mm to about 3 mm, and the piezoelectric elements 310a, 310b each have an outer diameter $D_{310}$ of from about 5 mm to about 15 mm and a thickness $t_{310}$ of from about 0.1 mm to about 1 mm.

In one embodiment, the acoustic communication carrier frequency is about 20 KHz or higher. In one embodiment, the acoustic communication carrier frequency is about 40 KHz. In one embodiment described in Table 2 below, the diaphragm portion 56 and the acoustic transducer active portion 302 are configured to be resonant at the 40 KHz communication carrier frequency, as determined by the following system characteristics:

TABLE 2

| Diaphragm 56 | |
| --- | --- |
| Material | Titanium |
| Thickness $t_{56}$ | 0.3 mm |
| Ring member 90 | |
| Material | CMW 1000 tungsten alloy |
| Inner diameter $D_{90}$ | 16 mm |
| Height $H_{90}$ | 2 mm |
| Pin member 300 | |
| Material | 303 stainless steel |
| Outer diameter $D_{300}$ | 2.5 mm |
| Height $H_{300}$ | 2.26 mm |
| Pin pad 318 | |
| Material | 303 stainless steel |
| Outer diameter | 3.75 mm |
| Height | 0.3 mm |
| Disk member 306 | |
| Material | 303 stainless steel |
| Outer diameter $D_{306}$ | 11.6 mm |
| Thickness $t_{306}$ | 0.5 mm |
| Piezoelectric elements 310a, 310b | |
| Material | PZT 5K3 |
| Outer diameter $D_{310}$ | 8 mm |
| Thickness $t_{310}$ | 0.3 mm (each) |

For any of the foregoing embodiments, the design of the transducer elements and the diaphragm portion may be optimized to achieve the desired frequency response characteristics (i.e., transmit sensitivity, receive sensitivity, or increased bandwidth) using any predictive technique known in the art. One such technique is the iterative optimization method described in co-pending and commonly assigned U.S. Provisional Patent Application 60/820,055 titled "Ultrasonic Transducer for a Metallic Cavity Implanted Medical Device," the contents of which are incorporated herein by reference for all purposes.

In the embodiments shown and described above, the piezoelectric elements and disk members of the transducers 60, 260 have generally circular shapes. In other embodiments, these elements could take on different shapes, e.g., rectangular, beam-shaped, circular, annular, or triangular. Similarly, while in the embodiments illustrated above, the diaphragm portion 56 of the housing 50 has a generally circular shape, in other embodiments, the diaphragm portion 56 could take a non-circular shape. Additionally, the diaphragm portion 56 and the active transducer portions need not have the same general shape.

In the foregoing embodiments, the invention has been described with respect to implantable medical devices such as pacemakers and defibrillators, but could be adapted for use in any other implantable medical device, such as an insulin pump, neurostimulator, drug delivery system, pain management system, heart or lung sound sensor, or any other implantable medical device. The remote device 16 can be any type of chronically implanted device or remote sensor adapted to deliver therapy or monitor biological functions, such as pressure sensor, glucose level monitor, a pulmonary sound sensor, volume sensor, satellite pacing device, or any other remote sensing or therapy-delivering device, and can be located anywhere in the body adapted for sensing a desired biological parameter or delivering therapy. A plurality of remote devices 16 could be implanted throughout the body and in wireless acoustic communication with each other and with another implanted medical device.

Figure 4:
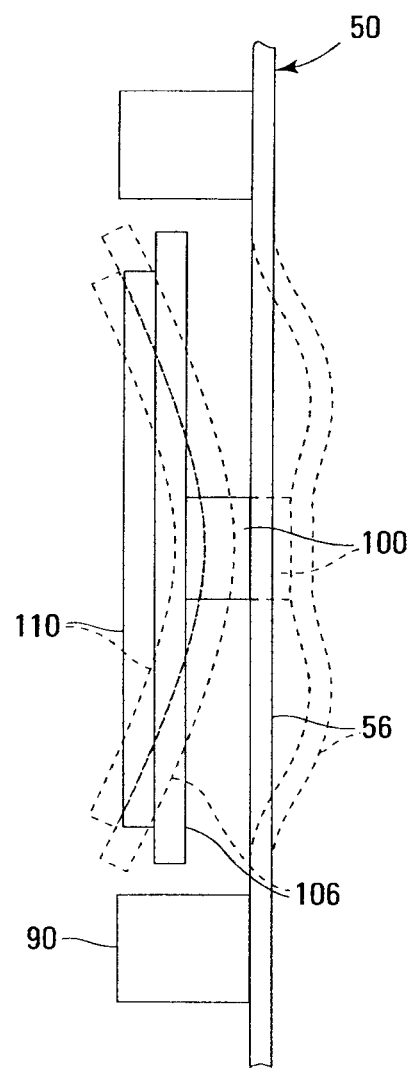
FIG. 4 is a schematic illustration of the operation of the acoustic transducer of FIGS. 2A and 2B.

FIG. 4 is a schematic depiction of the operation of the acoustic transducer 60 according to one embodiment of the present invention. In FIG. 4, the undeformed state of the transducer 60, i.e., its state in the absence of an applied AC voltage to the piezoelectric element 110 or external acoustic waves impinging on the diaphragm portion 56 of the housing 50, is shown in solid lines, while the deformed state of the transducer 60 is shown in dashed lines. As shown in FIG. 4, in the undeformed state of the transducer 60, the flexible disk 106 and the piezoelectric element 110 are arranged generally parallel to the wall of the housing 50. Application of an AC voltage across the piezoelectric element 110 causes the peripheral portions of the piezoelectric element 110 and the flexible disk 106 to deflect relative to their central portions (i.e., the portions proximate the pin member 100) at the frequency of the applied voltage. This deformation of the active transducer portion 102 causes the pin member 100 to translate and vibrate, thereby causing deformation of the diaphragm portion 56 of the housing 50. In the illustrated embodiment, the ring member 90 operates to define the extent of the diaphragm portion 56. In other embodiments, as discussed above, the ring member 90 may be omitted, and the diaphragm portion 56 may be otherwise defined, e.g., by a bump or recess in the housing wall surrounded by a relatively rigid wall portion. As shown, the pin member 100 does not itself deform, but instead simply translates or deflects along a line substantially transverse to the wall of the housing 50. Accordingly, the pin member 100 operates to support the active transducer portion 102 and to mechanically couple the active transducer portion 102 and the diaphragm portion 56.

The novel design of the transducer 60 results in maximum deformation of the peripheral portions of the flexible disk member 106 when the AC voltage is applied at a frequency corresponding to the resonance frequency of the active transducer portion 102. Where the resonance frequencies of the active transducer portion 102 and the diaphragm portion 56 are substantially equal, maximum deformation/vibration of both the diaphragm portion 56 and the active transducer portion 102 will result, thereby maximizing the transmit sensitivity of the acoustic transducer 60. Additionally, those skilled in the art will appreciate that the same principles will apply with respect to the response of the transducer 60 to external acoustic waves impinging upon the diaphragm portion 56. That is, where the resonance frequencies of the active transducer portion 102 and the diaphragm portion 56 are substantially matched and correspond to the carrier frequency of the impinging acoustic waves, maximum deformation/vibration of both the diaphragm portion 56 and the active transducer portion 102 will result, thereby maximizing the receive sensitivity of the acoustic transducer 60.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device comprising:
a housing defining a hermetically sealed chamber, the housing including a diaphragm portion with an inner surface, the diaphragm portion having a first resonance frequency;
an acoustic communication circuit within the chamber; and
an acoustic transducer within the chamber including:
a substantially rigid pin member having a first end attached to the inner surface in the diaphragm portion and a second end opposite the first end; and
an active portion coupled to the second end of the pin member, the active portion being electrically coupled to the acoustic communication circuit and having a second resonance frequency;
wherein the pin member offsets the active portion from the diaphragm portion to allow deformation of the active portion such that the first resonance frequency can be configured independently of the second resonance frequency; and
wherein the pin member is configured to transmit induced mechanical vibrations between the diaphragm portion of the housing and the active portion of the acoustic transducer, wherein the pin member has an outer diameter that is smaller than an outer diameter of the active portion.

2. The device of claim 1 wherein the diaphragm portion, the acoustic communication circuit, and the acoustic transducer form an acoustic communication system, and wherein the first and second resonance frequencies are selected so as to control at least one frequency response characteristic of the acoustic communication system.

3. The device of claim 2 wherein the frequency response characteristic is a transmit sensitivity.

4. The device of claim 1 wherein the first and second resonance frequencies are substantially equal.

5. The device of claim 4 wherein:
the active portion includes:
a generally planar, flexible disk member having a first surface and a second surface opposite the first surface; and
first and second generally planar, annular piezoelectric elements attached to and electrically isolated from the first and second surface of the disk member, respectively, and electrically coupled to the communication circuit; and
the second end of the pin member is attached to the second surface of the disk member.

6. The device of claim 5 wherein one or more of the pin member, the disk member, the first and second piezoelectric elements, and the diaphragm portion are configured such that first and second resonant frequencies are substantially equal.

7. The device of claim 6 wherein the acoustic communication circuit is adapted to apply an AC voltage to the piezoelectric elements and to thereby cause the piezoelectric element to vibrate at the first resonance frequency.

8. The device of claim 7 wherein the first and second resonance frequencies are about 40 KHz.

9. An implantable medical device comprising:
a housing defining a hermetically sealed chamber, the housing including a diaphragm portion with an inner surface, the diaphragm portion having a first resonance frequency;
an acoustic communication circuit within the chamber; and
an acoustic transducer within the chamber including:
a substantially rigid pin member having a first end attached to the inner surface in the diaphragm portion and a second end opposite the first end; and
an active portion coupled to the second end of the pin member, the active portion being electrically coupled to the acoustic communication circuit and having a second resonance frequency;
wherein the active portion further includes:
a generally planar, flexible disk member having a first surface and a second surface opposite the first surface;
first and second generally planar, annular piezoelectric elements attached to and electrically isolated from the first and second surface of the disk member, respectively, and electrically coupled to the communication circuit; and
the second end of the pin member is attached to the second surface of the disk member;
wherein one or more of the pin member, the disk member, the first and second piezoelectric elements, and the diaphragm portion are configured such that the first and second resonant frequencies are substantially equal; and
wherein the acoustic communication circuit is adapted to apply an AC voltage to the piezoelectric elements causing the piezoelectric elements to vibrate at the first resonance frequency.

10. An implantable medical device comprising:
a housing defining a hermetically sealed chamber, the housing including a diaphragm portion with an inner surface, the diaphragm portion having a first resonance frequency;
an acoustic communication circuit within the chamber; and
an acoustic transducer within the chamber including:
a substantially rigid pin member having a first end attached to the inner surface in the diaphragm portion and a second end opposite the first end; and
an active portion coupled to the second end of the pin member, the active portion being electrically coupled to the acoustic communication circuit and having a second resonance frequency;
wherein the active portion further includes:
a generally planar, flexible disk member having a first surface and a second surface opposite the first surface;
first and second generally planar, annular piezoelectric elements attached to and electrically isolated from the first and second surface of the disk member, respectively, and electrically coupled to the communication circuit; and
the second end of the pin member is attached to the second surface of the disk member;
wherein one or more of the pin member, the disk member, the first and second piezoelectric elements, and the diaphragm portion are configured such that the first and second resonant frequencies are substantially equal; and wherein the acoustic communication circuit is adapted to apply a time varying voltage to the piezoelectric elements causing the piezoelectric elements to vibrate at the first resonance frequency.

* * * * *